United States Patent
Sahm et al.

(10) Patent No.: US 8,911,772 B2
(45) Date of Patent: Dec. 16, 2014

(54) RELEASE LINER OR PROTECTIVE SHEET HAVING A SLIT COVERED BY ANOTHER LAYER FOR USE IN ADHESIVE LAMINATES

(75) Inventors: Hans-Dieter Sahm, Ingelbach (DE); Heinrich Thoeing, Bad Neuenahr-Ahrweiler (DE); Wolfgang Laux, Diez (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 566 days.

(21) Appl. No.: 12/602,172

(22) PCT Filed: May 27, 2008

(86) PCT No.: PCT/EP2008/004185
§ 371 (c)(1),
(2), (4) Date: Nov. 30, 2009

(87) PCT Pub. No.: WO2008/148477
PCT Pub. Date: Dec. 11, 2008

(65) Prior Publication Data
US 2010/0178343 A1  Jul. 15, 2010

(30) Foreign Application Priority Data
Jun. 4, 2007  (DE) .......................... 10 2007 025 973

(51) Int. Cl.
*A61F 13/00* (2006.01)
*A61K 9/70* (2006.01)
*A61F 13/02* (2006.01)

(52) U.S. Cl.
CPC ............... *A61F 13/02* (2013.01); *A61F 13/008* (2013.01); *A61K 9/7023* (2013.01); *A61F 13/0259* (2013.01); *A61K 9/703* (2013.01); *A61K 9/7053* (2013.01)

USPC .......................................... 424/448; 424/443

(58) Field of Classification Search
None
See application file for complete search history.

(56) References Cited

U.S. PATENT DOCUMENTS

| 5,336,162 | A | 8/1994 | Ota et al. |
| 5,891,463 | A | 4/1999 | Bello et al. |
| 6,464,821 | B1 * | 10/2002 | Phillips et al. ............. 156/304.1 |
| 2005/0037059 | A1 | 2/2005 | Miller, II |
| 2005/0228340 | A1 * | 10/2005 | Cleary et al. .................... 604/46 |

FOREIGN PATENT DOCUMENTS

| DE | 33 44 335 A1 | 6/1985 |
| DE | 199 25 338 A1 | 12/2000 |
| EP | 0 040 862 A1 | 12/1981 |
| JP | 9056745 A | 3/1997 |
| JP | 9238975 A | 9/1997 |
| JP | 2000-254164 * | 9/2000 .............. A61F 13/02 |

(Continued)

*Primary Examiner* — Kevin S Orwig
(74) *Attorney, Agent, or Firm* — ProPat, L.L.C.

(57) ABSTRACT

The invention relates to laminate segments equipped or coated with an adhesive matrix, particularly transdermal therapeutic systems having formulations strongly tending to leak adhesive. The inventive laminate segments include a matrix, with or without a back layer, a protective layer on the adhesive side of the matrix, provided with a cut as a peel-off aid, and a cover film partially coated with adhesive, applied to the protective film, which overlaps the cut in the protective film using the adhesive-free part thereof. The cover film prevents a leakage of the adhesive through the cut, and therefore a gluing together of the laminate segments to the packaging material thereof, without having an adverse effect on the function of the cut as a peel-off aid. Such laminate segments can be produced without the use of any intermediate carriers.

6 Claims, 2 Drawing Sheets

(56) References Cited

FOREIGN PATENT DOCUMENTS

| | | |
|---|---|---|
| JP | 3115629 | 11/2005 |
| WO | WO 02/089717 A1 | 11/2002 |
| WO | WO 2004/054638 A2 | 7/2004 |
| WO | WO 2007067363 A2 | 6/2007 |

* cited by examiner

RELEASE LINER OR PROTECTIVE SHEET HAVING A SLIT COVERED BY ANOTHER LAYER FOR USE IN ADHESIVE LAMINATES

CROSS-REFERENCE TO RELATED APPLICATIONS

This application is being filed under Rule 1.371 as a National Stage Application of pending International Application No. PCT/EP2008/004185 filed May 27, 2008, which claims priority to parent application German Patent Application No. 10 2007 025 973.7, filed Jun. 4, 2007. Both International Application No. PCT/EP2008/004185 and German Patent Application No. 10 2007 025 973.7 are hereby incorporated by reference herein in their entirety.

FIELD OF THE INVENTION

The present invention relates to adhesively furnished laminate or substrate sections whose adhesive side is provided with a protective covering. Said laminate or substrate sections are preferably transdermal therapeutic systems (TTS), more particularly therapeutic (i.e., containing active ingredient) patches.

BACKGROUND OF THE INVENTION

The production and use of adhesive laminate sections is known. Thus, for example, in the majority of cases, in a TTS, the adhesively furnished side, i.e., the side which in use adheres to the skin of the patient, is covered with a protective sheet, referred to as a release liner, in order to prevent the sections sticking to one another or to the external packaging. Typically, moreover, the protective sheet is provided with a cut, usually a central cut, which allows easy peeling of the sheet in at least two sections and therefore acts as a peeling aid. Systems of this kind are described in DE 3344335 A1, for example.

The adhesive of the adhesively furnished side of a laminate section or TTS of this kind, however, possesses a flow behavior which is dependent on the viscosity at room temperature and which is referred to as cold flow. One possible consequence of this is that, when the sections are stored, the adhesive emerges at the cut edge and, as a result, there is extremely disadvantageous sticking of the sections to one another or to the surrounding packaging, usually a pouch of packaging material.

One possible solution to this problem is described in DE 19925338 A1. There, the protective sheet on the pressure-sensitive adhesive layer is constructed so as to consist of two sheet sections which overlap in the region of the cut edge. However, particularly in the case, for example, of TTS products with formulations that have a high propensity toward emergence of adhesive, this measure does not in all cases prevent sticking of TTS products to the packaging. Moreover, the production of such products proves to be capable of improvement. In the course of their production, the TTS laminate, composed of backing layer, matrix, and intermediate cover, is contour-cut through the backing layer and matrix, and, after the remaining laminate has been removed, the diecut TTS are transferred individually by means of the intermediate carrier/cover to a new protective sheet (release liner). For preventing the emergence of adhesive, this protective sheet has an overlap in the region of the cut edge. This process is susceptible to fault, since a large number of materials must be simultaneously moved and precisely positioned. A further disadvantage is that the intermediate carrier must be removed and disposed of.

SUMMARY OF ADVANTAGEOUS EMBODIMENTS OF THE INVENTION

It was an object of the present invention, therefore, to provide storage-stable, adhesively furnished laminate sections, more particularly storage-stable TTS products, in which, or in whose production, the disadvantages known from the prior art are avoided.

DETAILED DESCRIPTION OF ADVANTAGEOUS EMBODIMENTS OF THE INVENTION

Figure 1:
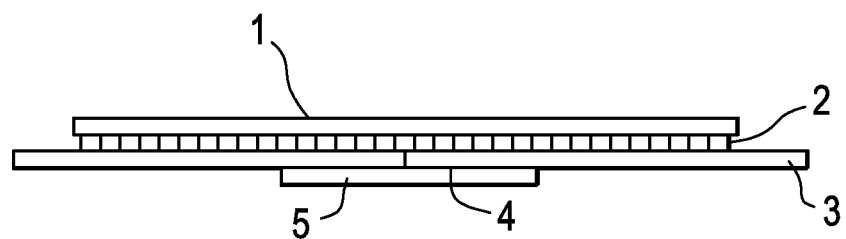
FIG. 1 is cross-sectional view of an exemplary laminate construction in accordance with the invention.

This object is achieved by the adhesively furnished laminate sections of the invention, comprising a matrix with or without a backing layer, which are characterized in that, on the adhesive side or layer of the matrix, they have a protective sheet, which as a peeling aid has a slit which is covered by a cover sheet (cover strip) applied to the protective sheet.

The construction of this cover strip is preferably such that it fully covers the slit in the protective sheet and is coated on one side with adhesive so that it bonds to the protective sheet. The cover strip is mounted so as not to impair the function of the slit in the actual protective sheet as a peeling aid. In other words, the cover strip is not coated completely with adhesive, and the part that is coated with adhesive is located only on one side of the slit. Preferably, therefore, the cover sheet is provided only over about half of its width with adhesive. In principle it is possible, for the cover strip, to use any suitable adhesive, such as, for example, pressure-sensitive adhesives based on natural rubbers and synthetic rubbers, polyacrylates, polyesters, polychloroprenes, polyisobutenes, polyvinyl ethers, and polyurethanes, which are used in combination with additives such as resins, plasticizers and/or antioxidants. Preference is given to using a silicone adhesive. This applies in particular to TTS products of the invention, since the majority of active drug ingredients have only a very low solubility in these silicone adhesives. It is preferred, furthermore, for the back of the cover strip to be coated with a barrier layer which is unable to bond to the adhesive of the cover strip. This applies in particular to TTS products with cover strips coated with silicone adhesive. Suitable materials for such barrier layers are, for example, polyethylene terephthalates and polyethylenes.

In one preferred embodiment the size of the cover sheet corresponds to the size of the actual protective sheet, which in turn may be greater than the actual laminate section or the matrix. In this case, protective sheet and cover sheet project beyond the actual laminate section at its margins; this may serve as an additional peeling aid for the protective sheet, and likewise corresponds to a preferred embodiment of the present invention.

The term "slit" in the actual protective sheet is to be interpreted broadly, i.e., it is not confined, for example, to one linear slit per laminate section. Instead, all geometric forms and patterns (e.g., a plurality of slits) are encompassed here. Examples of such are disclosed in DE 3344335 A1, whose United States equivalent is U.S. Pat. No. 4,587,146. In that case the cover sheet, and the regions of its coating with adhesive, are to be adapted accordingly.

The present invention accordingly embraces adhesively furnished laminate sections of any kind (such as, for example, sticking plasters, adhesive labels, self-adhesive postage stamps, etc.), preferably in the character of a TTS. These sections are composed in general of a plurality of layers and comprise a matrix (with or without a backing layer) having an adhesively furnished side or layer, adjacent to which there is a protective sheet with slits, and thereupon an adhesive-coated cover sheet, which covers the slit, preferably completely. In the form of a TTS, a laminate section of this kind generally comprises a backing layer, an adhesively furnished matrix comprising active ingredient (optionally with separate pressure-sensitive adhesive layer) for application to the skin of the patient, a protective sheet provided with a slit, and a cover sheet with layer of adhesive. In the case of the stated laminate sections, further layers may be included, or the stated elements may comprise different layers. The present invention can be employed widely and in particular can be used with all adhesively furnished TTSs.

FIG. 1 shows an example of the construction of a laminate section (1) of the invention. The key is as follows: (2) matrix, (3) protective sheet (release liner), (4) layer of adhesive on cover sheet, and (5) cover sheet.

The present invention also encompasses a method of producing the laminate sections or TTS products (TTS) of the invention, comprising the steps of:

a) providing the protective sheet of an adhesively furnished laminate with a slit, b) contour-cutting the laminate sections without severing the protective sheet, c) removing the remaining material between the laminate sections, d) applying the cover sheet, precoated with adhesive, to the protective sheet, and e) cutting out the laminate sections.

Taking as an example a TTS composed of backing layer, matrix, and protective sheet, the process of the invention will be elucidated in more detail, without being confined to this embodiment. In contrast to the prior art described, the protective sheet of the initial laminate now acts no longer only as an intermediate carrier which must later be disposed of, but instead is already part of the end product. The TTS laminate is drawn from a roll and first kiss-cut from its underside (protective sheet side) in such a way that the protective sheet is provided in lengthwise direction with a linear slit, in such a way that matrix and backing layer remain intact. In a further step, which takes place continuously, a contour cut is made through the backing layer and the matrix, with the protective sheet remaining intact, and subsequently the remaining material, comprising backing layer and matrix, can be removed (matrix-stripped). Thereafter the cover sheets, precoated with contact adhesive, is applied as a narrow strip to the underside of the TTS, to the protective sheet. In this arrangement the cover sheet preferably covers the protective sheet of the TTS completely. After a subsequent transverse cut to cut out the individual laminate sections, the TTS sections may be dispensed directly into the external packaging, usually in the form of a sealed pouch. In contrast to the above-described production process of laminate sections with an overlapping protective sheet, the method of the invention no longer necessitates the supplying of further materials.

As stated, the cover sheet is not fully coated with adhesive, so as not to impose any adverse effect on the function of the slit in the protective sheet as a peeling aid. The preferred methods for the production of the cover sheet are, accordingly, roller-coating methods with blank zones from which the required cover strips can be produced by a simple roller cut. A multiplicity of materials are suitable in principle as the material for the cover sheet, such as, for example, siliconized polyethylene terephthalate, polyethylene terephthalate, polyethylene, and polypropylene. The material of the cover sheet preferably corresponds to the material used for the actual protective sheet.

Figure 2:
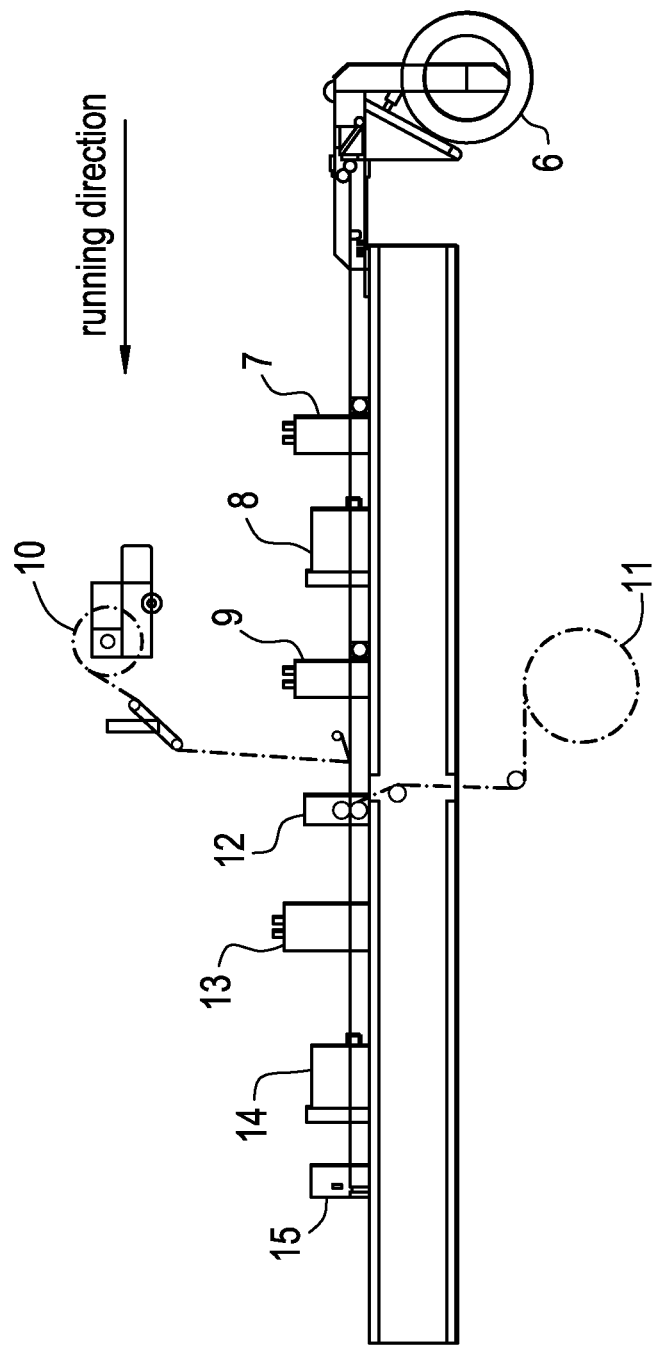
FIG. 2 illustrates an exemplary production method in accordance with the invention.

FIG. 2 shows one possible embodiment of the production method of the invention. Here the key is as follows: (6) laminate roll, (7) die for kiss-cutting the protective sheet to produce the slit, (8) forward draw device 1, (9) contour-cutting die, (10) winder for diecut stripping matrix, (11) unwinder for cover strip or cover sheet, (12) laminating station, 13 (embossing die), (14) forward draw device 2, and (15) transverse cutter.

The advantage of the production method of the invention lies in particular in the saving in terms of the final protective-sheet section to be newly supplied (avoidance of an intermediate carrier) and also in the easier operating regime, and hence in more rapid and more reliable handling of the product. The removal of the actual protective sheet is made even easier by the cover strip which is used (and which is bonded on one side of the slit).

Accordingly, this method, and the product construction according to the invention, can be employed in particular for all adhesively furnished products where there is a risk, owing to highly flowing adhesive compositions, of emergence of the adhesive through the protective-sheet slit, and hence a risk of unwanted sticking of products to one another or to their packaging.

The invention claimed is:

1. An adhesively furnished laminate section comprising a backing layer, a matrix having an adhesive side, and a protective sheet having first and second surfaces, said first surface of said protective sheet contacting the adhesive side of the matrix, wherein said protective sheet has a linear slit wherein the slit in the protective sheet serves as a peeling aid for the protective sheet and divides it into one or more segments of the same or different size and wherein the one or more segments directly abut one another; and a cover sheet partly coated with an adhesive is applied to the protective sheet on the second surface of said protective sheet, and the cover sheet fully covers the slit in the protective sheet, the cover sheet is partly coated with an adhesive; the adhesive-free part of the cover sheet covers the slit in the protective sheet and the adhesive-coated part of the cover sheet is located only on one side of the slit, and the laminate section is constructed as a transdermal therapeutic system.

2. The laminate section of claim 1, wherein the cover sheet fully covers the protective sheet.

3. The transdermal therapeutic system of claim 1, consisting of a backing layer, a matrix, a protective sheet with a slit, the protective sheet being on the adhesive side of the matrix, and a cover sheet which is applied to the protective sheet and which covers the slit in the protective sheet.

4. The transdermal therapeutic system of claim 3, wherein the cover sheet is coated with a silicone adhesive.

5. The transdermal therapeutic system of claim 3, wherein the cover sheet is provided with a barrier layer which does not stick to the adhesive of the cover sheet.

6. A method of producing a laminate section or transdermal therapeutic system of claim 1, comprising the steps of a) providing the protective sheet of an adhesively furnished laminate with a slit,
b) contour-cutting the laminate sections without severing the protective sheet,
c) removing the remaining material between the laminate sections,
d) applying the cover sheet, precoated with adhesive, to the protective sheet, and
e) cutting out the laminate sections.

\* \* \* \* \*